United States Patent
Yasumoto et al.

(10) Patent No.: US 11,443,837 B2
(45) Date of Patent: Sep. 13, 2022

(54) GENERATION OF TEST DATA FOR A DATA PLATFORM

(71) Applicant: INTERNATIONAL BUSINESS MACHINES CORPORATION, Armonk, NY (US)

(72) Inventors: Chikafumi Yasumoto, Tokyo (JP); Yutaka Oishi, Kawasaki (JP); Munetaka Ohtani, Fujisawa (JP); Jiayun Zhu, Tokyo (JP); Kumiko Maeda, Chuo-ku (JP); Yoshinori Tahara, Yamato (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 434 days.

(21) Appl. No.: 15/816,077

(22) Filed: Nov. 17, 2017

(65) Prior Publication Data
US 2019/0155989 A1    May 23, 2019

(51) Int. Cl.
*G16H 10/60* (2018.01)
*G06F 16/28* (2019.01)
*G16H 50/70* (2018.01)
*G16H 10/40* (2018.01)

(52) U.S. Cl.
CPC ......... *G16H 10/60* (2018.01); *G06F 16/285* (2019.01); *G16H 50/70* (2018.01); *G16H 10/40* (2018.01)

(58) Field of Classification Search
None
See application file for complete search history.

(56) References Cited

U.S. PATENT DOCUMENTS

| | | | |
|---|---|---|---|
| 7,233,938 B2 * | 6/2007 | Carus | G06Q 50/22 705/2 |
| 9,405,778 B2 | 8/2016 | Yin et al. | |
| 9,411,712 B2 | 8/2016 | Feynman | |
| 9,552,266 B2 | 1/2017 | Taylor, III et al. | |
| 2010/0318481 A1* | 12/2010 | Feynman | G06F 11/3684 706/12 |
| 2010/0324929 A1* | 12/2010 | Petrasich | G06F 19/328 705/2 |
| 2014/0372149 A1 | 12/2014 | Friese et al. | |
| 2015/0339442 A1* | 11/2015 | Oleynik | G06F 19/324 705/3 |
| 2016/0259701 A1* | 9/2016 | Masser | G06F 11/2635 |

(Continued)

OTHER PUBLICATIONS

Raza, Ali, "Test Data Extraction and Comparison with Test Data Generation", All Graduate Theses and Dissertations, Aug. 1, 2011, Paper 982, Utah State University, Logan, Utah.

(Continued)

*Primary Examiner* — James Trujillo
*Assistant Examiner* — J Mitchell Curran
(74) *Attorney, Agent, or Firm* — Michael Best & Friedrich LLP (57) ABSTRACT

Test data may be generated by classifying a plurality of medical records of patients into a plurality of groups, based on at least an execution characteristic of a processing program that processes the medical records, and generating test data including at least a part of the plurality of medical records based on proportions of the number of the medical records classified into the plurality of groups.

13 Claims, 7 Drawing Sheets

(56) References Cited

U.S. PATENT DOCUMENTS

2017/0091201 A1* 3/2017 Chabot ................. G06F 16/164
2018/0011972 A1* 1/2018 Rajan ..................... G16H 50/20

OTHER PUBLICATIONS

United States Patent Office Action for U.S. Appl. No. 16/416,936 dated Sep. 29, 2020 (13 pages).
United States Patent Office Action for U.S. Appl. No. 16/416,936 dated Mar. 30, 2021 (13 pages).

* cited by examiner

| Record ID | X | Y |
|---|---|---|
| XYZ111 | 10 | -5 |
| XYZ112 | -1 | 2 |
| XYZ113 | 9 | 3 |
| XYZ114 | -4 | -1 |

GENERATION OF TEST DATA FOR A DATA PLATFORM

BACKGROUND

Technical Field

The present invention relates to generation of test data for a data platform.

Related Art

When constructing a data platform such as a cloud platform, it is necessary to evaluate the data platform with test data before the release. In order to improve the quality of the data platform, it is desirable to prepare a large amount of test data that is the same as or similar to actual data. However, an amount of available actual data for the test may be limited for some reasons in certain scenarios. On the other hand, randomly sampled test data may cause a skew in training of the data platform.

SUMMARY

According to an aspect of the present invention, provided is a method, including classifying a plurality of medical records of patients into a plurality of groups, based on at least an execution characteristic of a processing program that process the medical records, and generating test data including at least a part of the plurality of medical records based proportions of the number of the medical records classified into the plurality of groups.

The aspect may also include an apparatus performing the method, and a computer program product storing instructions embodied on a computer-readable medium or programmable circuitry, for causing a processor or the programmable circuitry to perform the method. The summary clause does not necessarily describe all features of the embodiments of the present invention. Embodiments of the present invention may also include sub-combinations of the features described above.

DETAILED DESCRIPTION

Hereinafter, example embodiments of the present invention will be described. The example embodiments shall not limit the invention according to the claims, and the combinations of the features described in the embodiments are not necessarily essential to the invention.

Figure 1:
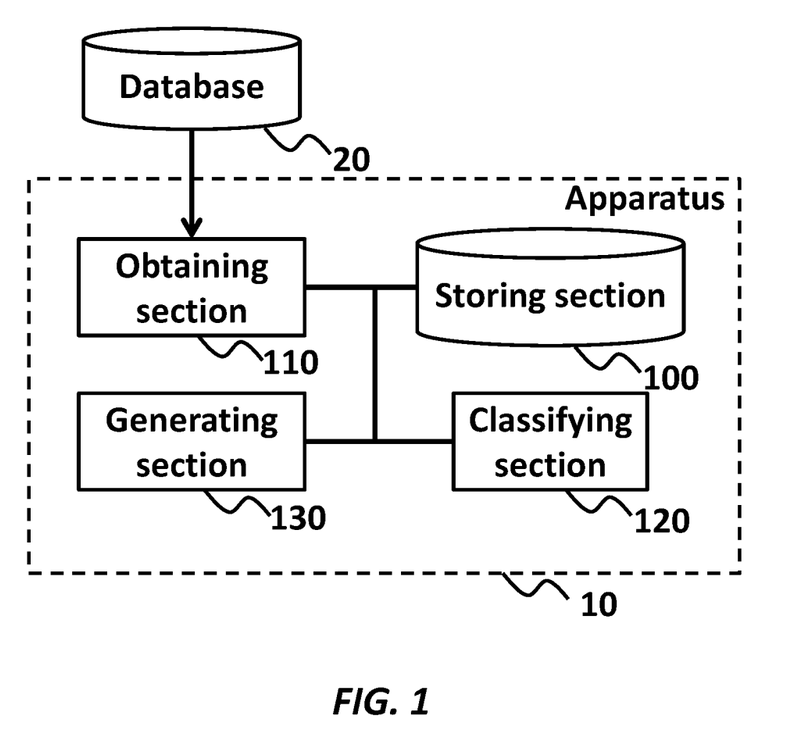
FIG. 1 shows an exemplary configuration of an apparatus 10, according to an embodiment of the present invention.

FIG. 1 shows an exemplary configuration of an apparatus 10, according to an embodiment of the present invention. The apparatus 10 may obtain an original set of medical records and generate test data by sampling at least a part of the medical records so as to preserve characteristics of the original set of medical records.

The apparatus 10 may include a processor and/or programmable circuitry. The apparatus 10 may further include one or more computer readable mediums collectively including instructions. The instructions may be embodied on the computer readable medium and/or programmable circuitry. The instructions, when executed by the processor or the programmable circuitry, may cause the processor or the programmable circuitry to operate as a plurality of operating sections.

Thereby, the apparatus 10 may be regarded as including a storing section 100, an obtaining section 110, a classifying section 120, and a generating section 130.

The storing section 100 may store information used for the processing that the apparatus 10 performs. The storing section 100 may also store a variety of data/instructions used for operations of the apparatus 10. One or more other elements in the apparatus 10 (e.g., the obtaining section 110, the classifying section 120, and the generating section 130) may communicate data directly or via the storing section 100, as necessary.

The storing section 100 may be implemented by a volatile or non-volatile memory of the apparatus 10. In some embodiments, the storing section 100 may store medical records, proportions, test data, and other data related thereto.

The obtaining section 110 may obtain a plurality of medical records of patients. In an embodiment, the medical record may be a record of a medical event of a patient. The obtaining section 110 may obtain the medical records from the storing section 100 or an external database, such as a database 20.

The classifying section 120 may classify the plurality of medical records of patients into a plurality of groups, based on at least an execution characteristic of a processing program that process the medical records. The processing program may be at least part of a program of a medical data platform.

The execution characteristic may represent how each medical record is treated in the medical data platform. In an embodiment, the execution characteristic may include a code pass through which the processing program processes the medical record.

The classifying section 120 may further classify the medical records in at least one group into a plurality of subgroups, by using one or more attributes of the medical records. In an embodiment, the one or more attributes may include at least one of size of an image file in the medical records, and a name of the image file in the medical records.

The generating section 130 may generate test data. The test data may include at least a part of the plurality of medical records based on proportions of the number of the medical records classified into the plurality of groups. In an embodiment, the generating section 130 may sample the medical records so as to target the proportions of the number of the medical records classified into the plurality of groups, in the test data.

Figure 2:
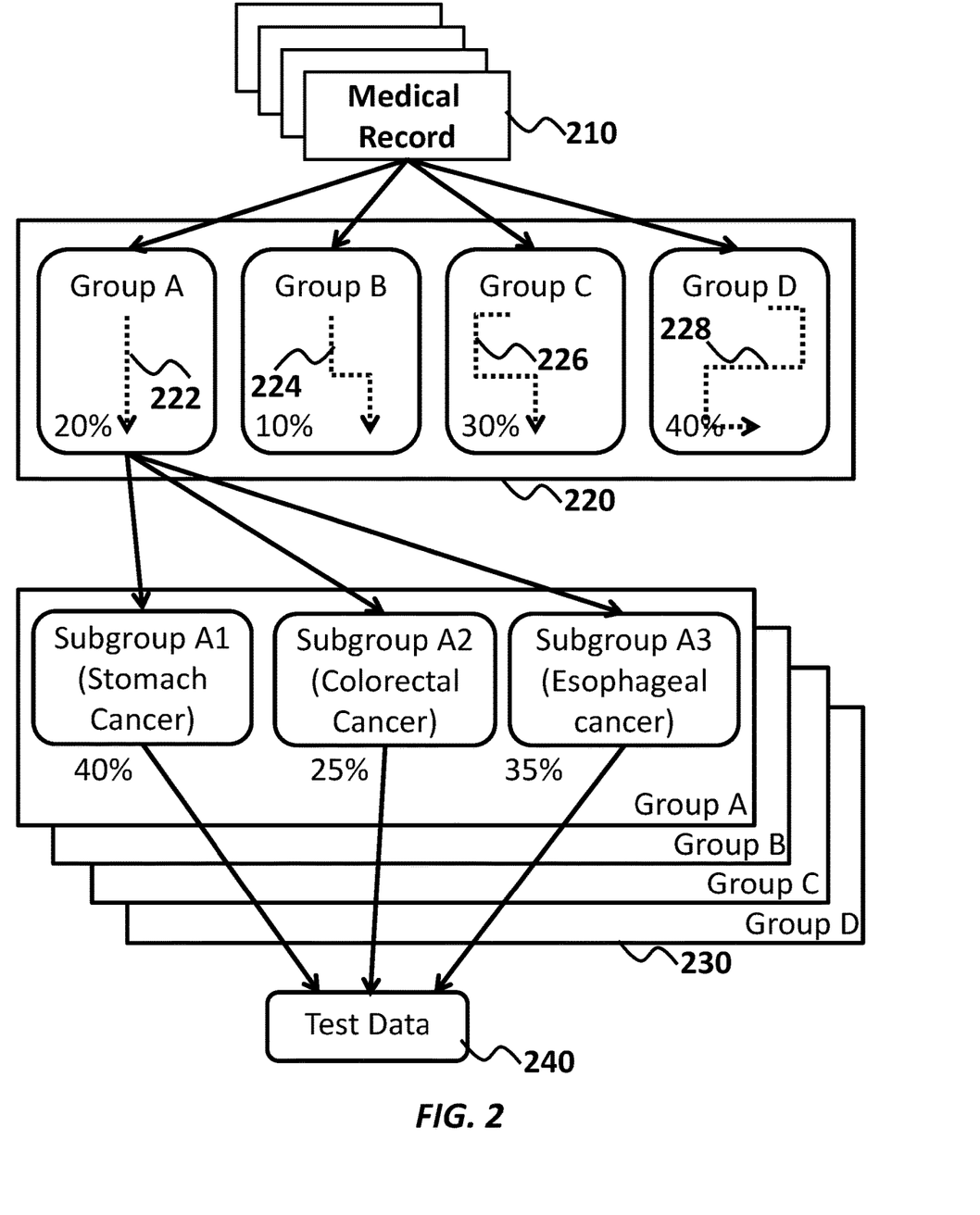
FIG. 2 shows a general concept of methods performed by the apparatus, according to an embodiment of the present invention.

FIG. 2 shows a general concept of methods performed by the apparatus, according to an embodiment of the present invention. In the embodiment, the obtaining section 110 may obtain a plurality of medical records 210. In the embodiment, the classifying section 120 may classify the plurality of medical records 210 into a plurality of groups 220. In the embodiment of FIG. 2, the plurality of groups 220 includes a group A, a group B, a group C, and a group D.

The medical records in each group may have a common, substantially common, or similar code path. In an embodiment, the medical records classified as the group A have a code pass 222, the medical records classified as the group B have a code pass 224, the medical records classified as the group C have a code pass 226, and the medical records classified as the group A have a code pass 228. In the embodiment of FIG. 2, the numbers of the medical records in the group A, the group B, the group C, and the group D are 20%, 10%, 30%, 40% to the total number of the medical records.

The classifying section 120 may further divide each group into a plurality of subgroups 230. The plurality of subgroups 230 of the group A includes a subgroup A1, a subgroup A2, and a subgroup A3.

The medical records in each subgroup may have close attributes. In an embodiment, the medical records in the subgroup A1 may be related to stomach cancer, the medical records in the subgroup A2 may be related to colorectal cancer, and the medical records in the subgroup A3 may be related to esophageal cancer. In the embodiment of FIG. 2, the numbers of the medical records in the subgroup A1, the subgroup A2, and the subgroup A3 are 40%, 25%, 35% to the number of the medical records in the group A.

The generating section 130 may generate test data 240 that has close characteristics to the original medical records 210. In an embodiment, the test data has about 20% of the medical records of the group A, about 10% of the medical records of the group B, about 30% of the medical records of the group C, and about 40% of the medical records of the group D. In an embodiment, the medical records classified as the group A in the test data 240 may have about 40% of the medical records of subgroup A1, about 25% of the medical records of subgroup A2, and about 35% of the medical records of subgroup A3.

Figure 3:
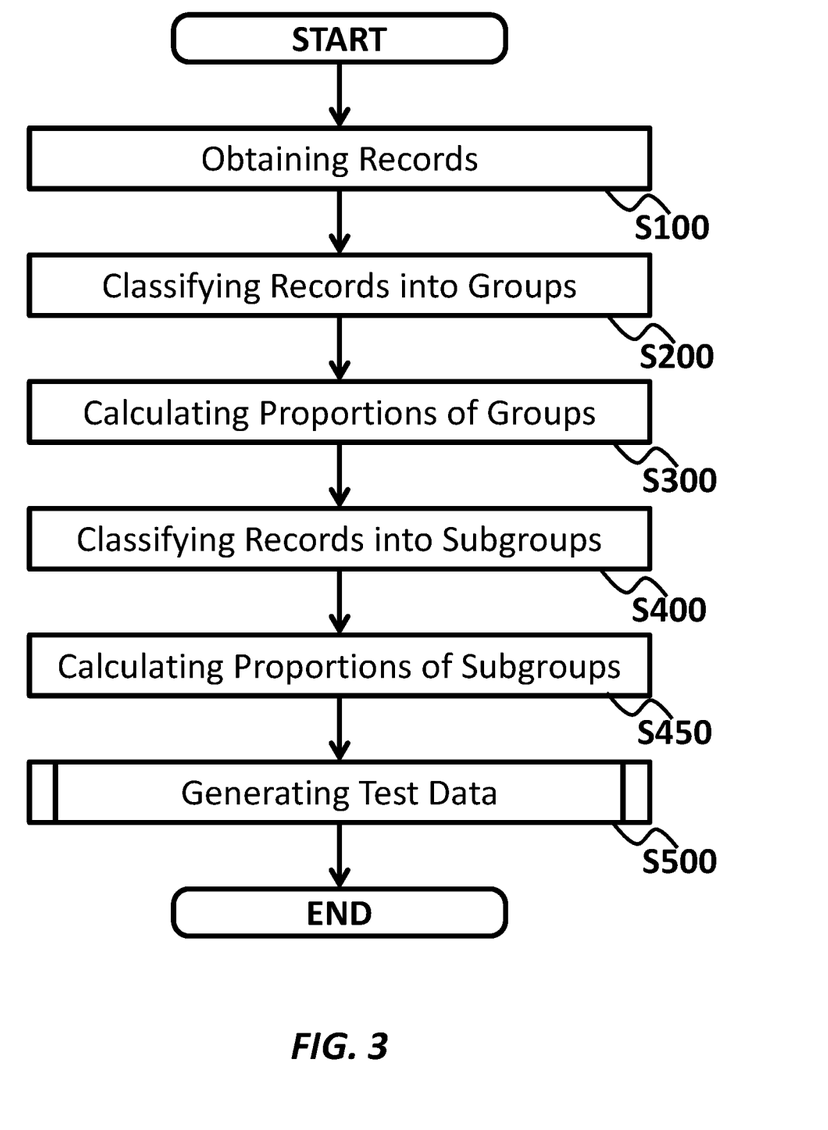
FIG. 3 shows an operational flow according to an embodiment of the present invention.

FIG. 3 shows an operational flow according to an embodiment of the present invention. The present embodiment describes an example in which an apparatus, such as the apparatus 10, performs operations from S100 to S500, as shown in FIG. 3.

At S100, an obtaining section such as the obtaining section 110 may obtain a plurality of medical records. The one or more attributes may include information that affects the code path of the medical record.

In an embodiment, the one or more attributes may relate to the medical event. For example, the one or more attributes may include a type of disease, a type of diagnosis, a type of medical device/institute, a result of diagnosis, a diagnostic image, a size of the diagnostic image, and so on.

The medical record may further include an ID of a patient and/or a medical institution or device, and/or a timestamp. The medical record may be a record of a patient which may be generated by a medical doctor or medical device.

At S200, a classifying section such as the classifying section 120 may classify the plurality of medical records obtained at S100 into a plurality of groups, based on at least an execution characteristic of a processing program that processes the medical records. In an embodiment, the classifying section may classify the plurality of medical records into the plurality of groups, each representing a specific type of code path.

In an embodiment, the classifying section may determine the code path of each medical record by actually running at least part of the processing program for each medical record. In another embodiment, the classifying section may determine the code path of each medical record by performing condition estimation for the one or more attributes of each medical record.

Figure 4:
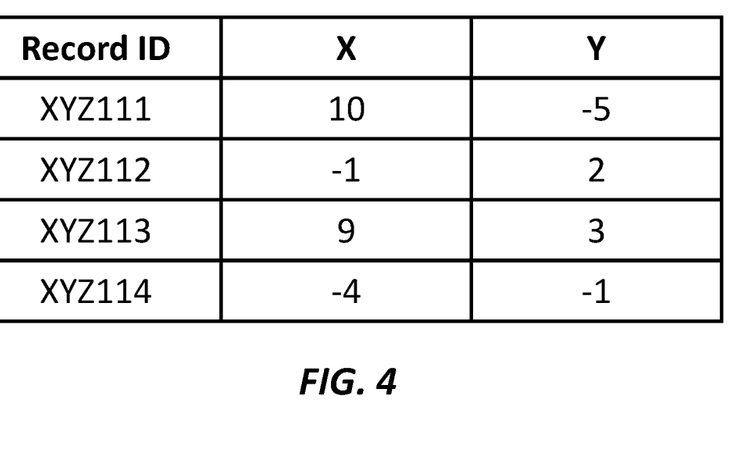
FIG. 4 shows attributes of medical records, according to an embodiment of the present invention.

FIG. 4 shows attributes of medical records, according to an embodiment of the present invention. FIG. 4 shows 4 medical records having IDs of XYZ111, XYZ112, XYZ113, and XYZ114. These medical records have an attribute X and an attribute Y. For example, the medical record "XYZ111" has a value of 10 in the attribute X, and a value of −5 in the attribute Y.

Figure 5:
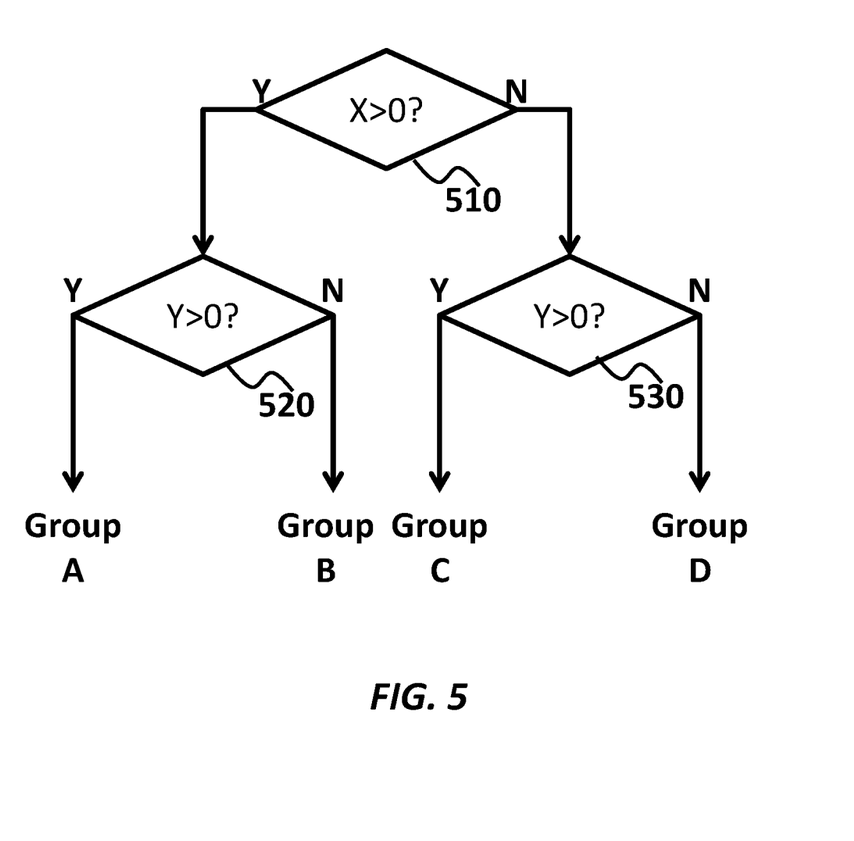
FIG. 5 shows condition estimation according to an embodiment of the present invention.

FIG. 5 shows condition estimation according to an embodiment of the present invention. The condition estimation includes a branch 510, a branch 520, and a branch 530. At the branch 510, if X>0, then a path goes to the branch 520, and if not, then a path goes to the branch 530. At the branch 520, if Y>0, then a code path is identified as Group A, and if not, then a code path is identified as Group B. At the branch 530, if Y>0, then a code path is identified as Group C, and if not, then a path is identified as Group D.

In an embodiment, the condition estimation such as shown in FIG. 5 may be prepared by analyzing the processing program. In the embodiment, the classifying section may perform the prepared condition estimation for the medical records. For example, the classifying section may classify the medical record "XYZ111" of FIG. 4 into Group B, classify the medical record "XYZ112" into Group C, classify the medical record "XYZ113" into Group A, and classify the medical record "XYZ114" into Group D, based on the condition estimation of FIG. 5.

At S300, the classifying section may calculate proportions of the plurality of groups. In the embodiment of FIG. 2, the classifying section may calculate a proportion of the number of the medical records classified as Group A (shown as 20%), a proportion of the number of the medical records classified as Group B (shown as 10%), a proportion of the number of the medical records classified as Group C (shown as 30%), and a proportion of the number of the medical records classified as Group D (shown as 40%).

At S400, the classifying section may further classify the medical records in at least one group of the plurality of groups into a plurality of subgroups, by using one or more attributes of the medical records.

In an embodiment, the classifying section may classify the medical records in a group into the plurality of subgroups, based on at least a distance of the one or more attributes of the medical records. The distance of the one or more attributes may be a distance of vectors representing the one or more attributes. The distance of the one or more attributes may be a distance between sentences (e.g., a diagnostic result written by a doctor or generated by a medical device) in the one or more attributes.

In an embodiment, the classifying section may weight each of the attributes of the medical records. For example, the classifying section may perform the classification for the subgroups by using clustering methods such as k-means algorithm, Support Vector Machine, and so on.

In an embodiment, the classifying section may classify the medical records in a group into the plurality of subgroups, based on at least predetermined criteria. For example, the classifying section may classify, among the medical records of Group A, the medical records that have information (e.g., a name of the image file of the medical record) relating to stomach cancer (e.g., diagnostic image of stomach, text including words relating to stomach cancer, etc.) as a subgroup representing Stomach Cancer (such as Subgroup A1 in FIG. 2). In another example, the classifying section may classify, among the medical records of Group B, the medical records that have the image file of which size is in a predetermined range, as a subgroup B1.

Criteria for the classification of subgroups may be the same or different among the plurality of groups. In an embodiment, the medical records of Group A may be classified into the subgroups in an aspect of a type of cancer, the medical records of Group B may be classified into the subgroups in an aspect of data amount.

In an embodiment, the classifying section may classify one medical record into one or more subgroups. For example, the classifying section may classify a medical record that reveals a possibility of stomach cancer and colorectal cancer into both Subgroup A1 and Subgroup A2.

In the embodiment of FIG. 2, the classifying section may classify not only the medical records of Group A into Subgroup A1, Subgroup A2, and Subgroup A3, but also the medical records of Group B and the medical records of Group C in a similar manner.

At S450, the classifying section may calculate proportions of the plurality of subgroups. In the embodiment of FIG. 2, the classifying section may calculate a proportion of the number of the medical records classified as Subgroup A1 (shown as 40%), a proportion of the number of the medical records classified as Subgroup A2 (shown as 25%), and a proportion of the number of the medical records classified as Subgroup A3 (shown as 35%).

At S500, a generating section such as the generating section 130 may generate test data including one or more medical records. In an embodiment, the generating section may perform sampling of the medical records obtained at S100 for the test data. Details of the operation of S500 are explained in relation to FIGS. 6-7.

Figure 6:
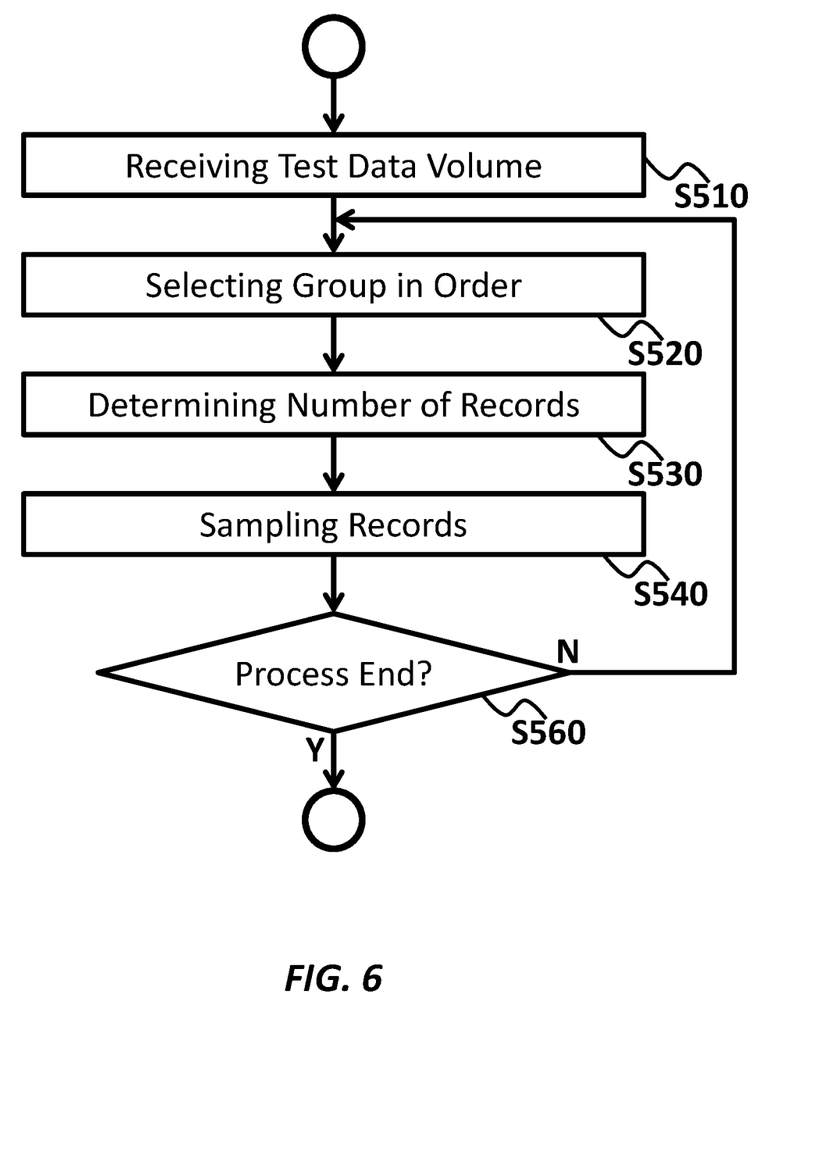
FIG. 6 shows a sub-flow of S500 according to an embodiment of the present invention.

FIG. 6 shows a sub-flow of S500 according to an embodiment of the present invention. The generating section may perform the operations from S510 to S560 at S500 in FIG. 3.

At S510, the generating section may receive information of a test data volume. In an embodiment, the generating section may receive a number of medical records included in the test data, data amount of the test data, data flowrate and test time of test data, and so on as the test data volume.

In a specific example, the generating section may receive 20 messages per second for 5 minutes as the volume of the test data. In the example, the generating section may determine to generate the test data including 6000 medical records by calculating 20×60×5. The number of medical records of the test data volume may be less than, the same as, or more than the number of the medical records obtained at S100.

At S520, the generating section may select a group in order. In the embodiment of FIG. 2, the generating section may select Group A at the first operation of S520, select Group B at the second operation of S520, select Group C at the third operation of S520, and select Group D at the fourth operation of S520. Hereinafter, a group selected at S520 may be referred to as "target group."

In an embodiment, the generating section may select only a part of the plurality of groups through the whole operation of S500. For example, the generating section may only select Group B to generate test data including only medical records of Group B.

The generating section may obtain the proportion of the number of the plurality of medical records in the target group calculated at S300. The proportion of the target group may be referred to as "target proportion."

At S530, the generating section may determine the number of the medical records to be included in the test data for the target group. The generating section may determine the number of the medical records for the target group by calculating a product of the target proportion and the test data volume received at S510.

The generating section may determine the number of the medical records for the target group by calculating a product of the number of medical records that is derived from the test data volume, and, a proportion of the target group. In an embodiment, when the test data volume is 6000 and the target group is Group A in FIG. 2, the generating section may determine that the number of the medical record for the target group is 6000×0.2=1200. Hereinafter the number of the medical records for the target group may be referred to as "target number."

At S540, the generating section may sample the target number of the medical records for the target group. If the number determined at S530 is 1200, then the generating section may sample 1200 medical records from the medical records that have been classified as Group A at S200.

The generating section may perform the sampling of the medical records for the target group such that proportions of the plurality of subgroups of sampled medical records are the same as, the substantially same, or approximated to the proportions of the plurality of subgroups calculated at S450.

In an embodiment, the generating section may perform the sampling of the medical records for the target group by sampling the target number of medical records at once.

In another embodiment, the generating section may perform the sampling of the medical records for the target group by iterating the sampling of at least one medical record until the number of sampled medical records reaches to the target number. In the embodiment, the generating section may perform the sampling of the at least one medical record such that proportions of the plurality of subgroups of sampled medical records come closer to the proportion of the subgroups in the classified medical records.

In a specific embodiment where the target number is 1200 and proportions of the subgroups A1, A2, A3 are 40%, 25%, 35% as shown in FIG. 2, the generating section may sample 480 medical records from the medical records of Subgroup A1, 300 medical records from the medical records of Subgroup A2, and 420 medical records from the medical records of Subgroup A3.

In an embodiment, the generating section may stochastically sample medical records for the plurality of subgroups. In the specific embodiment where the target number is 1200 and proportions of the subgroups A1, A2, A3 are 40%, 25%, 35%, the generating section may iterate sampling of medical record(s), from the medical records of Subgroup A1 with a probability of 40%, from the medical records of Subgroup A2 with a probability of 25%, and from the medical records of Subgroup A3 with a probability of 35%, until the number of sampled medical records reaches the target number.

In an embodiment, the generating section may sample at least one medical record for each subgroup. For example, if an estimated number of one subgroup is less than 1 (e.g., the target number is 100 and a proportion of the one subgroup is 0.5%), then the generating section may sample one medical record for the one subgroup. In another example, the generating section may not sample at least one medical record for a subgroup if an estimated number of the medical records for the subgroup is less than 1 or 0.5.

In an embodiment, the generating section may sample the same medical record twice or more at S540. In an embodiment, the generating section may not be allowed to sample the same medical record again unless all medical records have already been sampled.

At S560, the generating section may determine whether to end the process of FIG. 6. In an embodiment, the generating section may determine whether one or more predetermined groups have been selected at the operation of S520. For example, when the test data is to include medical records of all groups, the generating section may determine whether all groups (e.g., Group A, Group B, Group C, and Group D) have been selected at the operations of S520. For example, when the test data includes medical records of one group (e.g., Group A), the generating section may determine to end the process.

If the decision is positive, the generating section may end the operations, and if not, then the generating section may go back to the operation of S520. As explained above, the generating section may perform the operations of S530-S540 for each group of the plurality of groups.

In an embodiment, the generating section may provide all medical records sampled at the operation(s) of S540 as the test data after the operation of S560. In another embodiment, the generating section may stream medical records sampled during the operation(s) of S540 in real-time as the test data.

Figure 7:
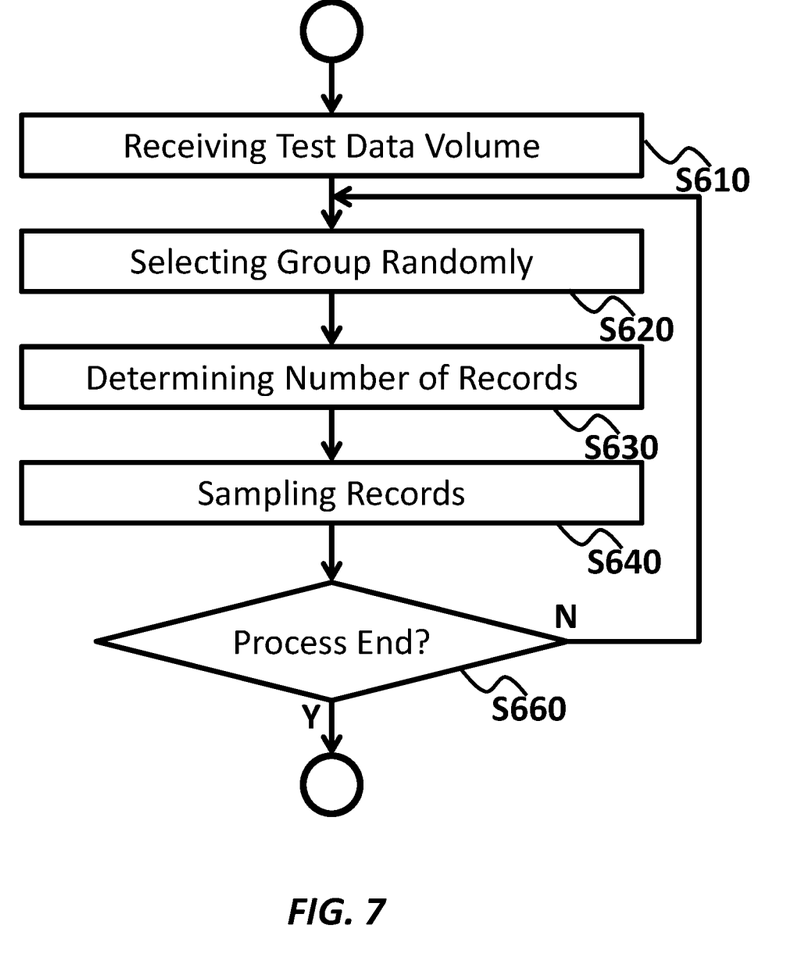
FIG. 7 shows a sub-flow of S500 according to another embodiment of the present invention.

FIG. 7 shows a sub-flow of S500 according to another embodiment of the present invention. The generating section may perform the operations from S610 to S660 at S500 in FIG. 3. The operations in FIG. 7 may at least partially correspond to the operations in FIG. 6. Explanations for features of the operations in FIG. 7 that are in common with those in FIG. 6 may be abbreviated.

At S610, the generating section may receive a test data volume. In an embodiment, the generating section may perform the operation of S610 in a similar manner as S510.

At S620, the generating section may randomly select a group. In a first sample, the generating section may select one of the plurality of groups (e.g., Group A, Group B, Group C, and Group D) with equal probability (e.g., 25%). In a second sample, the generating section may select one of the plurality of groups (e.g., Group A, Group B, Group C, and Group D) with probabilities corresponding to proportions of the groups (e.g., 20%, 10%, 30%, and 40%).

At S630, the generating section may determine the number of medical records to be included in the test data for the target group.

If the generating section adopts the first sample at S620, then the generating section may determine the number of medical records for the target group based on at least at least the target proportion and the test data volume received at S610, as explained in the operation of S530.

In the embodiment, the generating section may determine the number of medical record for the target group by calculating a product of the number of medical records that is derived from the test data volume, a proportion of the target group, and a sampling factor. In an embodiment, when the test data volume is 6000 and the target group is Group A, the generating section may determine that the target number is 6000×0.2×r, where r is a sampling factor defined as 0<r<=1. (1/r) may correspond to an expectation of the number of selections of each group.

If the generating section adopts the second sample at S620, the generating section may determine the number of medical records for the target group based on at least the test data volume received at S610, and an inverse number of the number of the plurality of groups.

In the embodiment, the generating section may determine the number of medical records for the target group by calculating a product of the number of medical records that is derived from the test data volume, and a sampling factor. In an embodiment, when the test data volume is 6000 and the target group is Group A, the generating section may determine that the target number is 6000×¼×r, where r is a sampling factor defined as 0<r<=1.

At S640, the generating section may sample the target number of medical records for the target group. In an embodiment, the generating section may perform the operation of S640 in a similar manner with S540.

At S660, the generating section may determine whether to end the process of FIG. 7.

In an embodiment, the generating section may determine whether a predetermined number (e.g., the number corresponding to the test data volume received at S610) of the medical records are sampled at S640.

In an embodiment, the generating section may determine whether a predetermined number of loops of S620-S660 have been processed.

In an embodiment, the generating section may determine whether one or more predetermined groups have been selected at the operations of S620. For example, when the test data includes medical records of all groups, the generating section may determine whether all groups (e.g., Group A, Group B, Group C, and Group D) have been selected at the operations of S620.

If the decision is positive, then the generating section may end the operations, and if not, then the generating section may go back to the operation of S620.

As explained above, the apparatus generates test data that has the same or similar proportions of original medical records, which represent actual medical records. The data platform may process the test data in a similar manner with the original medical records, in particular, from the aspect of data processing time, CPU resources, and/or storage capacity. Thereby, the data platform may be more accurately evaluated with the test data, in particular, from the aspect of performance and resource consumption.

In the embodiments explained above, the medical records are classified in levels of two layers: groups and subgroups. In some embodiments, the medical records are classified in a single level. In some embodiments, the medical records are classified in three or more levels.

Figure 8:
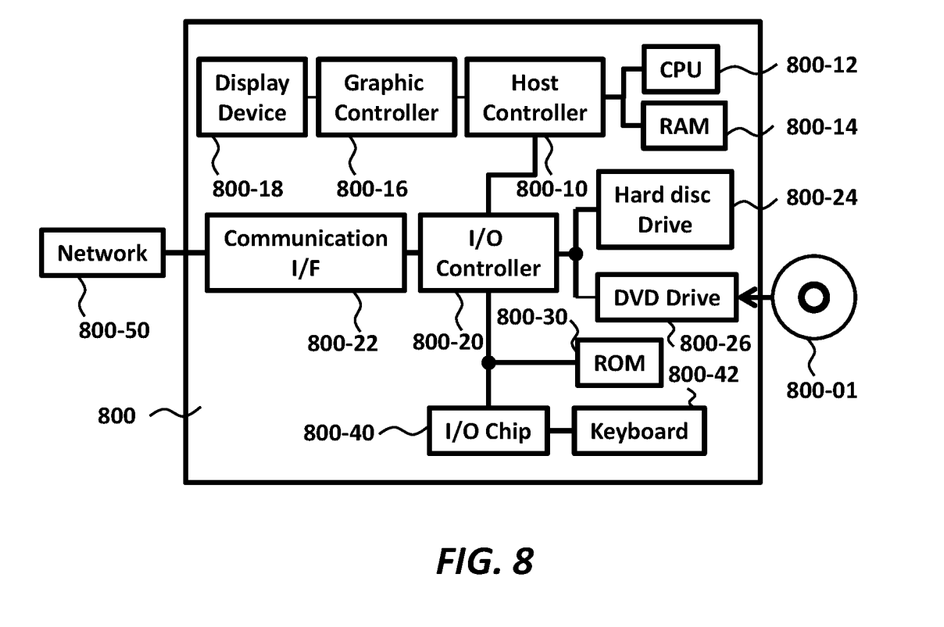
FIG. 8 shows an exemplary hardware configuration of a computer that functions as a system, according to an embodiment of the present invention.

FIG. 8 shows an exemplary hardware configuration of a computer configured for generating test data, according to an embodiment of the present invention. A program that is installed in the computer 800 can cause the computer 800 to function as or perform operations associated with apparatuses of the embodiments of the present invention or one or more sections (including modules, components, elements, etc.) thereof, and/or cause the computer 800 to perform processes of the embodiments of the present invention or steps thereof. Such a program may be executed by the CPU 800-12 to cause the computer 800 to perform certain operations associated with some or all of the blocks of flowcharts and block diagrams described herein.

The computer 800 according to the present embodiment includes a CPU 800-12, a RAM 800-14, a graphics controller 800-16, and a display device 800-18, which are mutually connected by a host controller 800-10. The computer 800 also includes input/output units such as a communication interface 800-22, a hard disk drive 800-24, a DVD-ROM drive 800-26 and an IC card drive, which are connected to the host controller 800-10 via an input/output controller 800-20. The computer also includes legacy input/output units such as a ROM 800-30 and a keyboard 800-42, which are connected to the input/output controller 800-20 through an input/output chip 800-40.

The CPU 800-12 operates according to programs stored in the ROM 800-30 and the RAM 800-14, thereby controlling each unit. The graphics controller 800-16 obtains image data generated by the CPU 800-12 on a frame buffer or the like provided in the RAM 800-14 or in itself, and causes the image data to be displayed on the display device 800-18.

The communication interface 800-22 communicates with other electronic devices via a network 800-50. The hard disk drive 800-24 stores programs and data used by the CPU 800-12 within the computer 800. The DVD-ROM drive 800-26 reads the programs or the data from the DVD-ROM 800-01, and provides the hard disk drive 800-24 with the programs or the data via the RAM 800-14. The IC card drive reads programs and data from an IC card, and/or writes programs and data into the IC card.

The ROM 800-30 stores therein a boot program or the like executed by the computer 800 at the time of activation, and/or a program depending on the hardware of the computer 800. The input/output chip 800-40 may also connect various input/output units via a parallel port, a serial port, a keyboard port, a mouse port, and the like to the input/output controller 800-20.

A program is provided by computer readable media such as the DVD-ROM 800-01 or the IC card. The program is read from the computer readable media, installed into the hard disk drive 800-24, RAM 800-14, or ROM 800-30, which are also examples of computer readable media, and executed by the CPU 800-12. The information processing described in these programs is read into the computer 800, resulting in cooperation between a program and the above-mentioned various types of hardware resources. An apparatus or method may be constituted by realizing the operation or processing of information in accordance with the usage of the computer 800.

For example, when communication is performed between the computer 800 and an external device, the CPU 800-12 may execute a communication program loaded onto the RAM 800-14 to instruct communication processing to the communication interface 800-22, based on the processing described in the communication program. The communication interface 800-22, under control of the CPU 800-12, reads transmission data stored on a transmission buffering region provided in a recording medium such as the RAM 800-14, the hard disk drive 800-24, the DVD-ROM 800-01, or the IC card, and transmits the read transmission data to network 800-50 or writes reception data received from network 800-50 to a reception buffering region or the like provided on the recording medium.

In addition, the CPU 800-12 may cause all or a necessary portion of a file or a database to be read into the RAM 800-14, the file or the database having been stored in an external recording medium such as the hard disk drive 800-24, the DVD-ROM drive 800-26 (DVD-ROM 800-01), the IC card, etc., and perform various types of processing on the data on the RAM 800-14. The CPU 800-12 may then write back the processed data to the external recording medium.

Various types of information, such as various types of programs, data, tables, and databases, may be stored in the recording medium to undergo information processing. The CPU 800-12 may perform various types of processing on the data read from the RAM 800-14, which includes various types of operations, processing of information, condition judging, conditional branch, unconditional branch, search/replace of information, etc., as described throughout this disclosure and designated by an instruction sequence of programs, and writes the result back to the RAM 800-14.

In addition, the CPU 800-12 may search for information in a file, a database, etc., in the recording medium. For example, when a plurality of entries, each having an attribute value of a first attribute is associated with an attribute value of a second attribute, are stored in the recording medium, the CPU 800-12 may search for an entry matching the condition whose attribute value of the first attribute is designated, from among the plurality of entries, and reads the attribute value of the second attribute stored in the entry, thereby obtaining the attribute value of the second attribute associated with the first attribute satisfying the predetermined condition.

The above-explained program or software modules may be stored in the computer readable media on or near the computer 800. In addition, a recording medium such as a hard disk or a RAM provided in a server system connected to a dedicated communication network or the Internet can be used as the computer readable media, thereby providing the program to the computer 800 via the network.

The present invention may be a system, a method, and/or a computer program product. The computer program product may include a computer readable storage medium (or media) having computer readable program instructions thereon for causing a processor to carry out aspects of the present invention. The apparatus of the embodiments of the present invention may include the computer readable medium and the processor or programmable circuitry operable to execute the instructions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to individualize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

As made clear from the above, the embodiments of the present invention enable to generate the test data having close characteristics with the medical records.

What is claimed is:

1. A computer program product including one or more computer readable storage mediums collectively storing program instructions that are executable by a processor or programmable circuitry to cause the processor or programmable circuitry to perform operations comprising:
   classifying, with a classifying program, a plurality of medical records of patients into a plurality of groups, based on at least an execution characteristic of a processing program that processes the medical records, wherein:
   the classifying program is distinct from the processing program,
   the execution characteristic represents how each medical record is treated when processed by the processing program,
   the execution characteristic includes a code pass and the processing program processes the medical records through the code pass,
   each group of the medical records represents a specific type of code pass, and
   the classifying of the plurality of medical records includes determining a code pass of each medical record through the processing program by identifying one or more branches in the processing program and performing a condition estimation through the one or more branches for one or more attributes of each medical record without actually running the processing program; and generating test data for testing the processing program, the test data including at least a part of the plurality of medical records based on proportions of the number of the medical records classified into the plurality of groups; and testing the processing program using the generated test data.

2. The computer program product of claim 1, the operations further comprising:

classifying the medical records in at least one group into a plurality of subgroups, by using the one or more attributes of the medical records.

3. The computer program product of claim 2, wherein the one or more attributes includes at least one of a size of an image file in the medical records, and a name of the image file in the medical records.

4. The computer program product of claim 3, wherein the classifying the medical records in at least one group into a plurality of subgroups includes classifying the medical records, based on at least a distance of the one or more attributes of the medical records.

5. The computer program product of claim 1, wherein the generating test data includes sampling the medical records so as to target the proportions of the number of the medical records classified into the plurality of groups, in the test data.

6. The computer program product of claim 2, wherein the generating test data includes:

determining the number of the medical records to be included in the test data for each group, and sampling the determined number of the medical records for each group.

7. The computer program product of claim 6, wherein the sampling includes sampling at least one medical record for each subgroup.

8. The computer program product of claim 6, wherein the sampling includes sampling at least one medical record such that proportions of the plurality of subgroups of the sampled medical records come closer to the proportion of the subgroups in the classified medical records.

9. An apparatus comprising:
the computer readable medium of claim 1; and
a processor or programmable circuitry operable to execute the instructions.

10. An apparatus comprising:
the computer readable medium of claim 2; and
a processor or programmable circuitry operable to execute the instructions.

11. An apparatus comprising:
the computer readable medium of claim 3; and
a processor or programmable circuitry operable to execute the instructions.

12. An apparatus comprising:
the computer readable medium of claim 4; and
a processor or programmable circuitry operable to execute the instructions.

13. An apparatus comprising:
the computer readable medium of claim 5; and
a processor or programmable circuitry operable to execute the instructions.

* * * * *